(12) United States Patent
Kozmann et al.

(10) Patent No.: US 11,375,940 B2
(45) Date of Patent: Jul. 5, 2022

(54) METHOD AND MEASURING ARRANGEMENT FOR MONITORING SPECIFIC ACTIVITY PARAMETERS OF THE HUMAN HEART

(71) Applicant: Gyorgy Zoltan Kozmann, Budapest (HU)

(72) Inventors: Gyorgy Zoltan Kozmann, Budapest (HU); Gyorgy Kozmann, Budapest (HU)

( * ) Notice: Subject to any disclaimer, the term of this patent is extended or adjusted under 35 U.S.C. 154(b) by 611 days.

(21) Appl. No.: 16/306,345

(22) PCT Filed: May 19, 2017

(86) PCT No.: PCT/HU2017/050017
§ 371 (c)(1),
(2) Date: Nov. 30, 2018

(87) PCT Pub. No.: WO2017/208040
PCT Pub. Date: Dec. 7, 2017

(65) Prior Publication Data
US 2021/0219901 A1    Jul. 22, 2021

(30) Foreign Application Priority Data

Jun. 1, 2016 (HU) .................................. P1600354

(51) Int. Cl.
*A61B 5/30* (2021.01)
*A61B 5/332* (2021.01)
(Continued)

(52) U.S. Cl.
CPC ............ *A61B 5/332* (2021.01); *A61B 5/0024* (2013.01); *A61B 5/0245* (2013.01); *A61B 5/271* (2021.01);
(Continued)

(58) Field of Classification Search
CPC ................................ A61B 8/00; A61B 5/0205
See application file for complete search history.

(56) References Cited

U.S. PATENT DOCUMENTS

2013/0041268 A1* 2/2013 Rimoldi ............. A61B 5/02125
600/479

FOREIGN PATENT DOCUMENTS

WO   WO-2011065516 A1 * 6/2011 ............. A61B 8/463
WO   WO2013184315     12/2013
(Continued)

OTHER PUBLICATIONS

PCT International Searching Authority; International Search Report and Written Opinion dated Jan. 15, 2018; entire document.

*Primary Examiner* — Michael J D'Abreu
(74) *Attorney, Agent, or Firm* — Allen, Dyer, Doppelt & Gilchrist, P.A.

(57) ABSTRACT

A method for monitoring specific activity parameters of the human heart, where ECG and PCG signal monitoring is performed simultaneously by at least two electrodes placed on the chest in such a way that the ECG signal is utilized as a reference time point during PCG monitoring, and monitoring is performed with a measuring unit consisting of a couple of measuring heads containing combined ECG and PCG electrodes, a controlling master measuring head and a slave measuring head performing synchronized implementation, and a computing evaluating unit which is in wireless data communication connection with the above unit and is capable of data processing. ECG and PCG signals are simultaneously monitored by two measuring heads, each comprising an ECG electrode and a PCG electrode, one of the measuring heads serving as a master measuring head and the other one of the measuring heads serving as a slave measuring head.

8 Claims, 4 Drawing Sheets

(51) Int. Cl.
*A61B 5/271* (2021.01)
*A61B 5/00* (2006.01)
*A61B 5/0245* (2006.01)
*A61B 7/04* (2006.01)

(52) U.S. Cl.
CPC .............. *A61B 5/6898* (2013.01); *A61B 7/04* (2013.01); *A61B 2562/06* (2013.01)

(56) References Cited

FOREIGN PATENT DOCUMENTS

| WO | WO2015112512 | 7/2015 |
| WO | WO2016061196 | 4/2016 |
| WO | WO2017120138 | 7/2017 |

* cited by examiner

METHOD AND MEASURING ARRANGEMENT FOR MONITORING SPECIFIC ACTIVITY PARAMETERS OF THE HUMAN HEART

CROSS-REFERENCE TO RELATED APPLICATION

This application is the § 371 National Stage Entry of International Application Serial No. PCT/HU2017/050017, filed on May 19, 2017, which claims the benefit of Hungarian Patent Application P1600354, filed on Jun. 1, 2016, the contents of which applications are herein incorporated by reference in their entirety.

FIELD OF THE INVENTION

The present invention relates to a method of monitoring specific activity parameters of the human, along with equipment and computer program products for the implementation of the method.

BACKGROUND OF THE INVENTION

Auscultation of the heart has a centuries-long history. The stethoscope, Laennec's epoch-making invention was an important milestone in 1816 as it was the first medical device. Since then modern medical technology has provided several new options for the examination of the heart (e.g. by ultrasound imaging). Nevertheless, inexpensive and widely available technologies based on auscultation have remained valuable tools in primary examinations, especially on the level of primary care.

The membrane sensor with the attached rubber tubing channels the sounds and finally the doctor gets the auscultation experience by direct vibration of the tympanic membrane via the eartip—it is still used widely. Its drawback is that the evaluation is subjective and it is difficult to teach.

The top products of the cutting-edge commercial solutions are digital stethoscopes which were launched a few years ago. These convert the vibration of the thoracic wall evoked by heart activity to electronic signals which allows the performance of optional signal processing steps, signal amplification, filtering, measurement of its parameters, visualization, forwarding, electronic storage, etc. The advances made in the last few decades are well characterized by the study of Yashaswini and Satyanarayana: "The design of an electronic Stethoscope—Review" published in International Conference on Computer Science and Informatics, 2012, Hyderabad issue, pp. 37-41. A more recent and detailed review is given in the article of Leng et al. BioMed Eng OnLine (2015) 14:66 DOI 10.1186/s12938-015-0056-y.

The type 3200 digital stethoscope of Littmann measures the vibrations of only one auscultation site at a time in accordance with the traditions, and at the same time, it tries to deprive the registered signals from the disturbing effect of the signal sources outside of the heart by filtering and the suppression of environmental noise. In order to prevent the subjective elements of expertise to limit correct diagnosis, it allows distance diagnostic consultation of the heart's acoustic signals—through networks with appropriate safety—between the physicians of optional geographic locations/institutes.

Although the Thinklabs One device (Thinklabs Electronic Stethoscope, http://www.thinklabmedical.com/) measures the vibrations of only one auscultation site by its novel capacitive sensor, the control elements placed on the measuring head allow the adjustment of the transfer band and amplification during measurement. The measured signals are stored on an external storage device following digital conversion, and an earphone may be attached for the physician during the examination. The smartphone or computer (PC) can display, store and/or forward the vibrations in time and time frequency range via Bluetooth connection.

The CardioSleeve device of Rijuven (http://www.rijuven.com/medicaldevices/cardiosleeve) is a supplementary unit which can be attached to any traditional stethoscope, allowing the use of older devices in the modern digital world. It stands out by the supposedly important innovation that via its dry ECG electrodes, the proprietary supplementary unit is able to record some of the ECG channels similar to Einthoven I, II or III leads along with the heart sound signals, allowing the correlation of the timing and duration of the sounds to the electronic (depolarization and repolarization) cycle leading to heart contraction and relaxation. However, the above mentioned three leads cannot be recorded simultaneously, but in three steps, by the rotation of the measuring head. As a further note, it has to be mentioned that the ECG electrodes of Rijuven's device fall outside of the standard points of measurement. Nevertheless, this solution allows the identification of the location, duration, and envelope of the sounds and murmurs in relation with the ECG signals that give a quantitative image of the electrical activity, and also allows the detection of arrhythmic or extra beats.

We found that at the level of known and commercially available devices, there is still no solution for the reliable and useful distinction of heart sounds and murmurs developing as a consequence of structural errors (such as not proper valve closure or opening). As regards research, e.g., the study of Akbari et al.: "Digital Subtraction Phonocardiography (DSP) applied to the detection and characterization of heart murmurs", Biomed Eng Online. 2011 Dec. 20; 10:109. doi: 10.1186/1475-925X-10-109 made a recommendation on a method of distinguishing heart murmurs from heart sounds, but as far as we know it was not utilized industrially. The proposed solution exploits the fact that heart sounds are repeated causally in each cycle, while murmurs are random due to the turbulent blood flow. In such cases, if the beginning of QRS wave (i.e. ventricular repolarization) is known in each cycle, after the subtraction of the heart sound signals in the consecutive cycles, the difference will show the murmurs' time function, and the heart sounds' time function will disappear during the creation of difference. The limitation of the method is that it does not define the beginning of the sounds, although it is an essential deficiency in terms of determining some of the often-used clinical parameters of heart activity, such as pre-ejection period (PEP) or left ventricular ejection time (LVET).

WO 2016061196 A2 describes systems, devices, and methods for capturing and outputting data regarding a bodily characteristic wherein in one embodiment, a hardware device can operate as a stethoscope with sensors to detect bodily characteristics such as heart sounds, lung sounds, abdominal sounds, and other bodily sounds and other characteristics such as temperature and ultrasound. The stethoscope can be configured to pair via a wireless communication protocol with one or more electronic devices, and upon pairing with the electronic device(s), can be registered in a network resident in the cloud and can thereby create a network of users of like stethoscopes. In particular, the document discloses a measuring arrangement for monitoring specific activity parameters of the human body, consisting of a measuring unit and an evaluating unit having a wireless communication connection with the measuring unit. Although it is possible to combine other sensors/electrodes with the used PCG sensors/electrodes, the spatial and/or temporal differences in the capturing can result in false measurements.

WO 2015112512 A1 describes portable electronic hemodynamic sensor systems for non-invasively monitoring cardiac health, in particular for extracting hemodynamic information, optionally employing portable electronic devices with optional user interface features for system implementation. The systems and methods may be employed for acquiring hemodynamic signals and associated electrophysiological data and/or analyzing the former or both in combination to yield useful physiological indicia or results, however, do not offer a possibility for a temporal assignment of the captured signals to be evaluated.

In WO 2013184315 A1 relating to enhanced auscultatory sensor and analysis for patient diagnosis, techniques and systems for detecting acoustic signals and generating phonocardiograms are described. In one example, a system includes an acoustic sensor configured to detect an acoustic signal from a heart of a patient. The system also includes another sensing module configured to detect an electrical signal from the heart of the patient via two or more electrodes and at least one processor configured to generate a composite phonocardiogram based the acoustic signal and the electrical signal detected over a plurality of cardiac cycles of the heart, wherein the composite phonocardiogram is generated for a representative cardiac cycle. The system may be provided in a single device or multiple devices configured to transmit information between the devices, however, multiple separate sensors or electrodes are used also in case of one single device.

In summary, commercial stethoscopes are not suitable for the detailed examination of the four heart valves in relation to the guiding ECG signal, that is, they are not able to accurately examine the opening and closure of the atrioventricular and ventriculo-aortic valves, that is, the valves of the right and left heart, to detect structural errors, and in pathological cases, the highly precise determination of the beginning and end of heart sounds and murmurs. As a result, the parameters used by clinicians for the assessment of the heart's mechanical and electromechanical activity are inaccurate.

SUMMARY OF THE INVENTION

The present invention is based on the notion that we can reliably determine the heart sound parameters, their relative timing and the additional cardiac murmurs that occur in case of imperfect heart function, with a reproducible result, if the mechanical vibrations of the body surface (PCG) and bioelectronic (ECG) signals initiating the mechanical activity are measured simultaneously, with more than one measuring head at the auscultation sites of the body surface, and it can be used as an anchor (reference) for error-free evaluation.

The set goal was achieved according to a method for monitoring specific activity parameters of the human heart comprising the steps of arranging measuring heads comprising electrodes of a measuring unit on the chest of a patient, monitoring predetermined parameters by two measuring heads placed on the chest, wherein monitoring comprises capturing an ECG signal by ECG electrodes and capturing a PCG signal by PCG electrodes, transmitting the captured signals wirelessly from the measuring unit to a computing evaluating unit, evaluating transmitted signals by means of the computing evaluating unit, utilizing the captured ECG signal as an anchor, that is, a reference time for the PCG monitoring, and displaying captured signals and/or evaluation results at least by means of a display means of the computing evaluating unit.

The step of performing monitoring further comprises performing monitoring the ECG and PCG signals simultaneously by two measuring heads, each comprising an ECG electrode and a PCG electrode, operating one of the measuring heads as a master measuring head and the other one of the measuring heads as a slave measuring head and controlling operation of the slave measuring head by the master measuring head. Monitoring is performed in the following order: capturing ECG and PCG signals between mitral and aortic auscultation points, capturing ECG and PCG signals between tricuspid and pulmonic points, determining a time difference between captured left and right ventricular mechanic contraction by capturing vibrations on the body surface between the aortic and pulmonic points, then capturing vibrations on the body surface between tricuspid and mitral points.

According to an embodiment of the present invention, a measuring arrangement for monitoring specific activity parameters of the human body, comprises a measuring unit including at least one measuring head comprising an ECG sensor and at least one measuring head comprising a PCG sensor, an evaluating unit having a wireless communication connection with the measuring unit.

The measuring unit comprises two measuring heads designed as master and slave measuring heads each comprising more than one ECG electrodes and PCG electrodes, one of the measuring heads is operated as a master measuring head and the other one of the measuring heads is operated as a slave measuring head, the master measuring head provides control of the slave measuring head for performing simultaneous capturing of the hearts electromechanical activity. The master measuring head comprises a communication stage providing wireless communication with the evaluating unit.

The invention is further presented in detail on the basis of an exemplary implementation and the introduction of a measuring arrangement with reference to the accompanying drawings as follows:

BRIEF DESCRIPTION OF THE DRAWINGS

FIG. 2 shows the exemplary measuring heads used in the measuring arrangement from below with the cable connection and combined electrodes between;

DETAILED DESCRIPTION OF PREFERRED EMBODIMENTS

As we mentioned earlier, the deficiency serving as the ground of our invention's development is the uncertainty of taking measurement parameters necessary for drawing conclusion, and one of the most important objective of the study is to eliminate such uncertainties. This could be reached by monitoring appropriate waves and setting corner/anchor time points.

Figure 1:
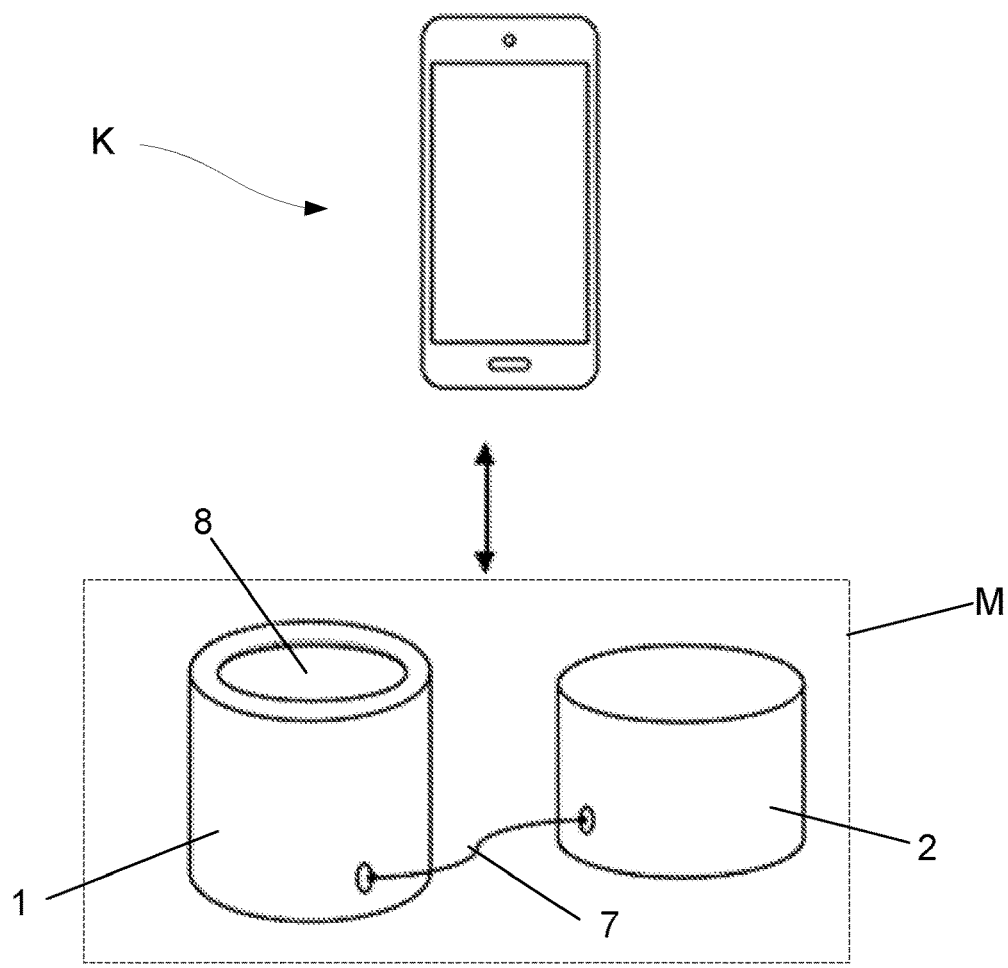
FIG. 1 shows the basic draft of the measuring arrangement according to the invention.

As it is shown in FIG. 1, the measuring arrangement according to the invention consists of two separated main parts: a measuring unit M and an evaluating unit K. The measuring unit M in the presented case consists of two measuring heads 1, 2 and the evaluating unit K consists of a smartphone. The two units have wireless connection, in this example via Bluetooth technology which is widespread and well-known in mobile communication. Of the two measuring heads 1, 2 comprising the measuring unit M, measuring head 1 is the so-called master head and measuring head 2 is the so-called slave head, and in this example there is a wire connection between them. The presented measuring arrangement with the measuring head pair 1, 2 combined with two electrodes—PCG and ECG—and being in a master-slave relationship, the smartphone being in wireless Bluetooth connection or other data-processing and archiving, that is, evaluating unit K with the characteristics described in the methodological chapter leads to a solution which eliminates the substantial deficiencies of the earlier solutions.

Figure 5:
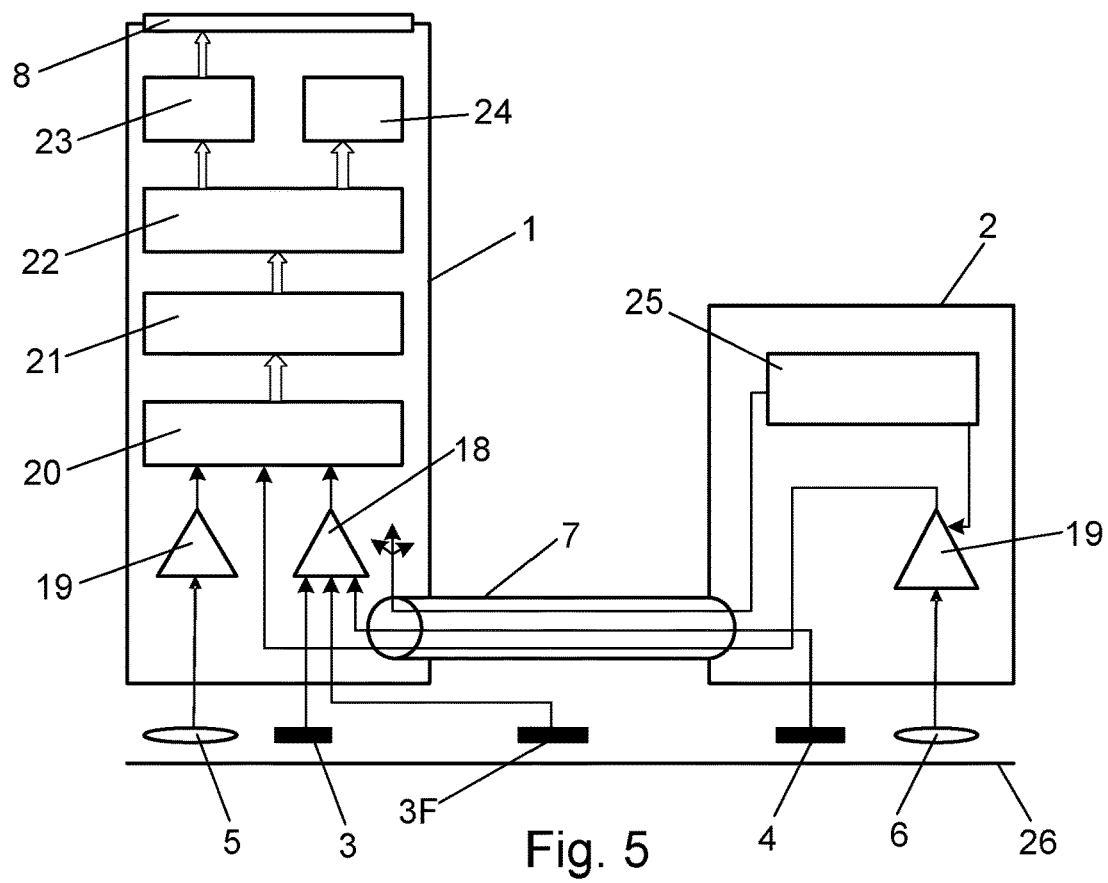
FIG. 5 shows the block scheme of the exemplary electronic setting of the "master" and "slave" measuring heads.

The measurement of the ECG and PCG signals takes place simultaneously in each cardiac cycle by measuring heads 1 and 2 which together contain a bipolar ECG sensor and two heart sound (PCG) electrodes 5, 6 implemented by dry (or possibly gel-containing) electrodes 3, 4, see FIG. 5. The sensory electrode 3 of the master 1 measuring head fulfils the function of the right leg electrode of the traditional 12-lead ECG, and electrode 4 of measuring head 2 is not exploited in the presented example. Communication between measuring head 1 and 2 takes place via a flexible multiconductor cable 7. The role of the cable 7 apart from ensuring an electrical connection between measuring heads 1 and 2, is to enable the physician to wear the device hung on his/her neck between examinations, similarly to a conventional stethoscope. A display 8 is in place for monitoring the recorded signals during measurement which in the example is positioned on the top of the master 1 measuring head, recessed into its case. The detailed numerical and/or graphic result of the computerized signal processing and evaluation can be presented on the display of the smartphone comprising the evaluating unit K. The combined setting of measuring heads 1 and 2 drafted here is a substantial element of the solution according to the invention.

Figure 3:
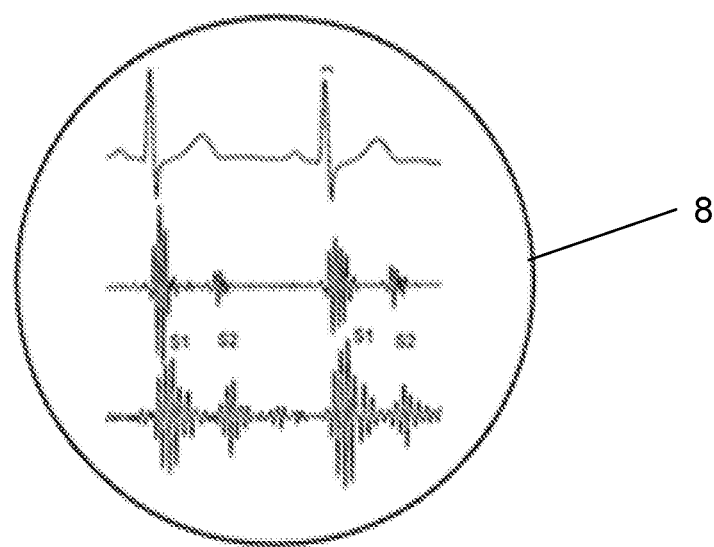
FIG. 3 shows the information appearing on the liquid-crystal display placed on the upper surface of the "master" measuring head according to FIG. 2.

The measuring heads 1 and 2 are not identical; measuring head 1 is more complex in terms of functionality, and it is the "master" head within the set, ensuring synchronized operation with the "slave" measuring head, along with the visual presentation of the ECG and PCG signals on the liquid-crystal display 8 during data collection as shown as an example in FIG. 3.

Considering that the valves represent the operation of the left ventricle and right ventricle in pairs, it is logical to simultaneously examine the physiologically "cohesive" two left ventricular and two right ventricular valves at the auscultation sites 9 through 12 (see FIG. 4) where the cardiac auscultation sites 9-12 are shown, and the ribs and sternum are also presented to facilitate anatomical orientation.

Further combinations allow the measurement of temporal and morphological differences between PCG components originating from the left and right side.

In order to ensure practical applicability, the invention is the development of a measuring head combination 1, 2 suitable for use on both men and women is required, regardless of their size, anatomical composition, and body posture. Due to the significant anatomical differences of the two sexes, the solution with two 1, 2 measuring heads connected by a multiconductor cable 7 is recommended by all means for routine examinations which allows the physician, relying on his or her knowledge of anatomy to place the electrodes of the measuring head set on the standard auscultation points without disturbing the patient. At the same time, in order to preserve the traditions of device sporting, the physician can carry the measurement head set 1, 2 according to the invention hung on his/her neck between examinations, similarly to a conventional stethoscope.

Considering that the signals of the measuring heads 1, 2 are recorded digitally, the results of the data collection can be evaluated by the physician acoustically as well as graphically in the form of time functions, similarly to ECG and PCG records, depending on his/her preference. The latter takes place on the display 8 built into the master 1 measuring head, see FIG. 3. The liquid-crystal display shown in FIG. 3 provides qualitative control option for checking the quality of the recorded signals during measurements and ensures that the physician does not have to look at the display of the smartphone or any other device.

The final graphic and/or numerical result of the signal processing is presented on the display of the smartphone comprising the evaluating unit K.

The measuring head set 1, 2 according to the invention ensures wireless, e.g. Bluetooth forwarding of the measured data to the evaluating unit K, e.g. a smartphone or database which performs more detailed analysis.

Figure 2:
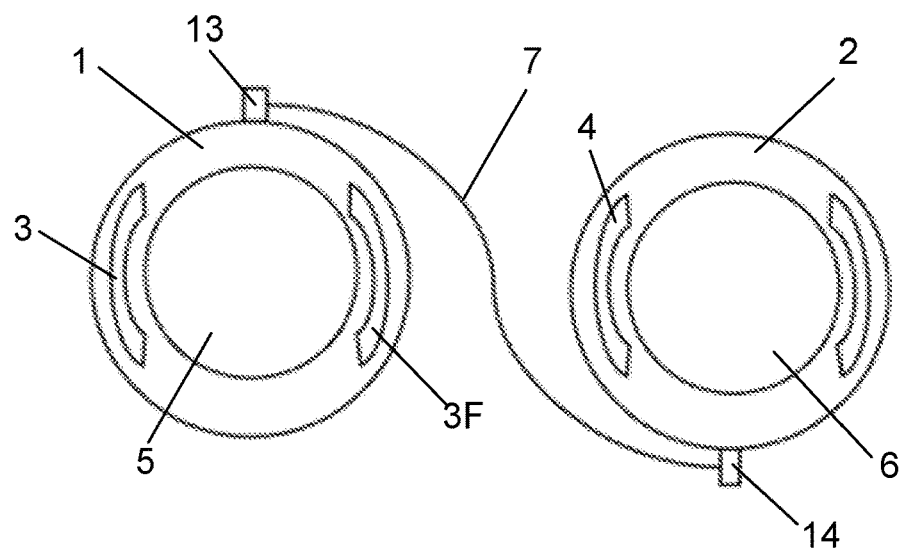

FIG. 2 shows the electrodes of measuring heads 1 and 2 from a bottom view, that is, from the direction of the human body surface. From below, there are ECG electrodes 3, 4 separated from each other and the electrodes 5, 6 detecting the vibrations of the chest, placed in an insulating case made of e.g. a plastic accepted and used in healthcare devices. The electronic connection between the cable 7 and the measuring heads 1, 2 is provided by decomposable multipole connectors 13, 14. Electrode 3F serves as the "right leg electrode" of the classic ECG lead system. The bipolar ECG measured by electrodes 3 and 4 has the following functions: determining the R-R distances 15 and QRS onset 17 indicated in FIG. 6 and based on the above data, establishing the beginning and end of the QRS wave and defining the QT distance 16.

Figure 6:
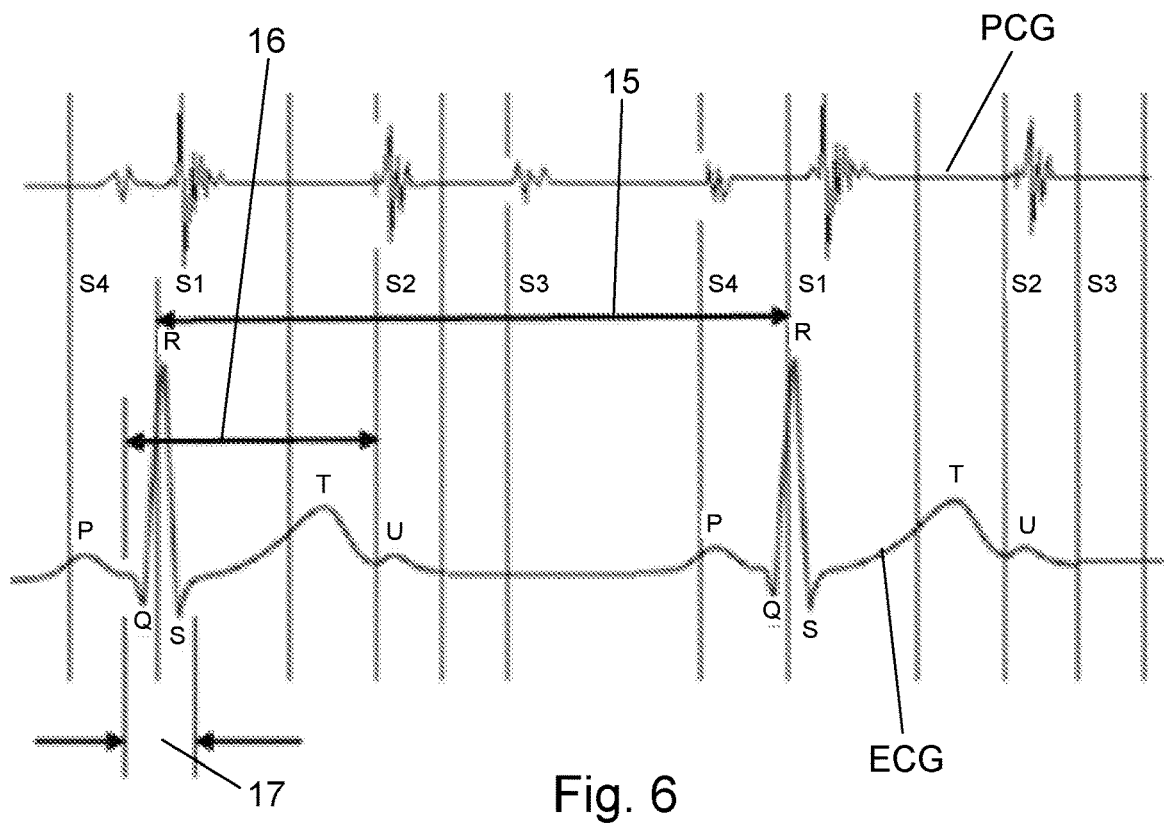
FIG. 6 shows the graphic view of the measurement parameters that were taken into consideration during the method according to the invention.

FIG. 6 explains the parameters mentioned in the scope of ECG measurements and processing. Based on a uniform international consensus, the waves detected on ECG are called P, Q, R, S, T, and U. Each wave represents the depolarization i.e. electronic activation or repolarization i.e. return to the baseline electronic state of a specific part of the heart. The QRS complex or ventricular wave shown on the figure, marking the rapid depolarization of the ventricles, consists of the small negative Q wave which is not always detectable, the positive R wave, having up to 10 mV amplitude, indicating the stimulation of the main mass of ventricular muscle, and a negative S wave. The depolarization of the total working ventricular musculature takes place during the QRS wave; its normal duration is 0.06-0.12 sec: of this, depolarization of the interventricular septum takes cca. 0.03 sec, and depolarization of the right and left ventricle takes 0.055 sec and 0.068 sec, respectively. The figure also shows the QT distance which is the total duration of ventricular muscle depolarization and repolarization combined. QT distance normalized against the heart rate should not be shorter than 0.36 sec and longer than 0.44 sec in physiologic cases.

During procession, the ECG signal can be used for the distinction between the so-called "majority" and "extra" beats. In accordance with the idea according to the invention, the moment of the beginning of QRS wave serves as a reference or anchor for the synchronous averaging of thoracic vibration signals. In case of an increased QRS length, the QRS parameters (see Oravecz et al: Dynamic Analysis of Heart Sounds in Right and Left Bundle-Branch Blocks, Circulation, 36, 275-283, 1967) promote the distinction between the left and right ventricular components of the first heart sound S1 during the summarization of the results.

FIG. 5 shows the block scheme of an exemplary electronic setting of the master and slave 1, 2 measuring heads. The figure shows a master 1 measuring head and a slave 2 measuring head. Both measuring heads 1, 2 include an ECG electrode 3, 4 known in itself by the professionals and a sensor 5, 6) capable of taking up mechanical vibrations which can be implemented with only a microphone or even by a MEMS acceleration detector. The master 1 measuring head includes the electronic unit processing the signals provided by the measuring head's ECG electrode and PCG electrode. In the presented example, it includes a multi-input 18 amplifying stage which can be feasible by a bipolar ECG amplifier and e.g. by a type AD8232 circuit known in the field, in accordance with the manufacturer's instructions. The 3F electrode indicates the ground electrode of the input 18 amplifying stage used for bipolar ECG amplifier, and it connects to the appropriate input of the amplifying stage 18. In addition, measuring head 1 includes the amplifying stage 19 connecting with electrode 5 belonging to measuring head 1 which is implemented with a type MCP607 dual operational amplifier in the present example. The output of amplifying stages 18 and 19 is connected with the multiplexer stage 20 and its output is connected with the analog-to-digital converter's 21 input which has a sampling frequency of at least 500 Hz, in this case as well. The analog-to-digital converter 21 in this example is implemented as a type ASDS1248 24-bit circuit and its output is connected in this example with an Atmega2560 type processor stage 22 which is well-known and working. The processor stage 22 can be more closely known from several instructions for use in accordance with the all-time needs; on one hand, it connects with the LCD 8 display through the memory stage 23, and on the other hand it is connected to the Bluetooth stage 24 allowing and providing wireless communication. In this latter case, it was implemented by a MicroChipRN42 type commercially available unit. The stored signals are forwarded via Bluetooth connection to the smartphone used as the evaluating unit for final processing showed in FIG. 7. We also symbolically presented the part of the body surface 26 where the auscultation sites 9-12 are located.

The ECG electrode belonging to the slave measuring head connects with the measuring head 1, and its sensor is connected to the input of the amplifying stage 19 already used in measuring head 1. In the presented example, amplifying stage 19 is identical with amplifying stage 18 used in measuring head 1, therefore it also consists of a type MCP607 operational amplifier. The output of amplifying stage 19 is connected to another output of the multiplexer stage 20 in measuring head 1, and this connection is made possible by the cable 7 connecting the two measuring heads 1, 2 with each other and in addition to forwarding signals, it also allows electronic energy supply of measuring head 1 in such a way that the battery 25 placed in measuring head 2 provides not only the supply of measuring head 2 but through one of the conductors of the cable 7 it also provides energy for measuring head 1 and ensures that its units and stages are also supplied.

The battery 25 is also selected in accordance with actual needs; and in the case of the presented design, we used a 3.7 V, 490 mA rechargeable battery.

The display may be for example a 2×16-character LCD display compatible with the Hitachi HD44780 display.

The case of measuring heads 1 and 2 shall be practically made of plastic, in this example it is PVC closed by a sensor ring on one end. In this sensor ring, there are two built-in ECG DRL circuits which are in connection with the conductive membrane connected to the sensor ring. A PCG sensor surface is set behind the conductive membrane which is adjacent to a printed circuit board holding analog elements. The battery 25 is placed on the other side of the printed circuit board—in the case of measuring head 2—and on the other side of the battery 25 is another digital printed circuit board which has a known but here not illustrated electronic connection with the display embedded into the end-surface of the measuring head case.

Figure 4:
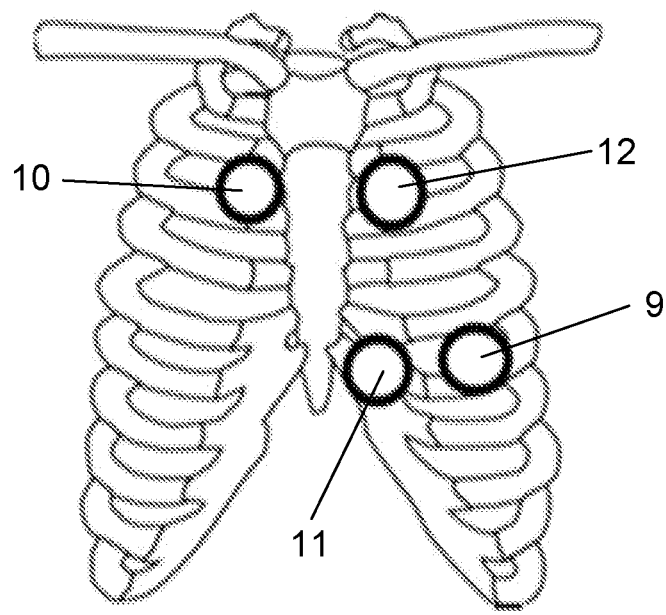
FIG. 4 shows the cardiac auscultation sites and also presents the ribs and sternum to facilitate anatomical orientation.
Figure 7:
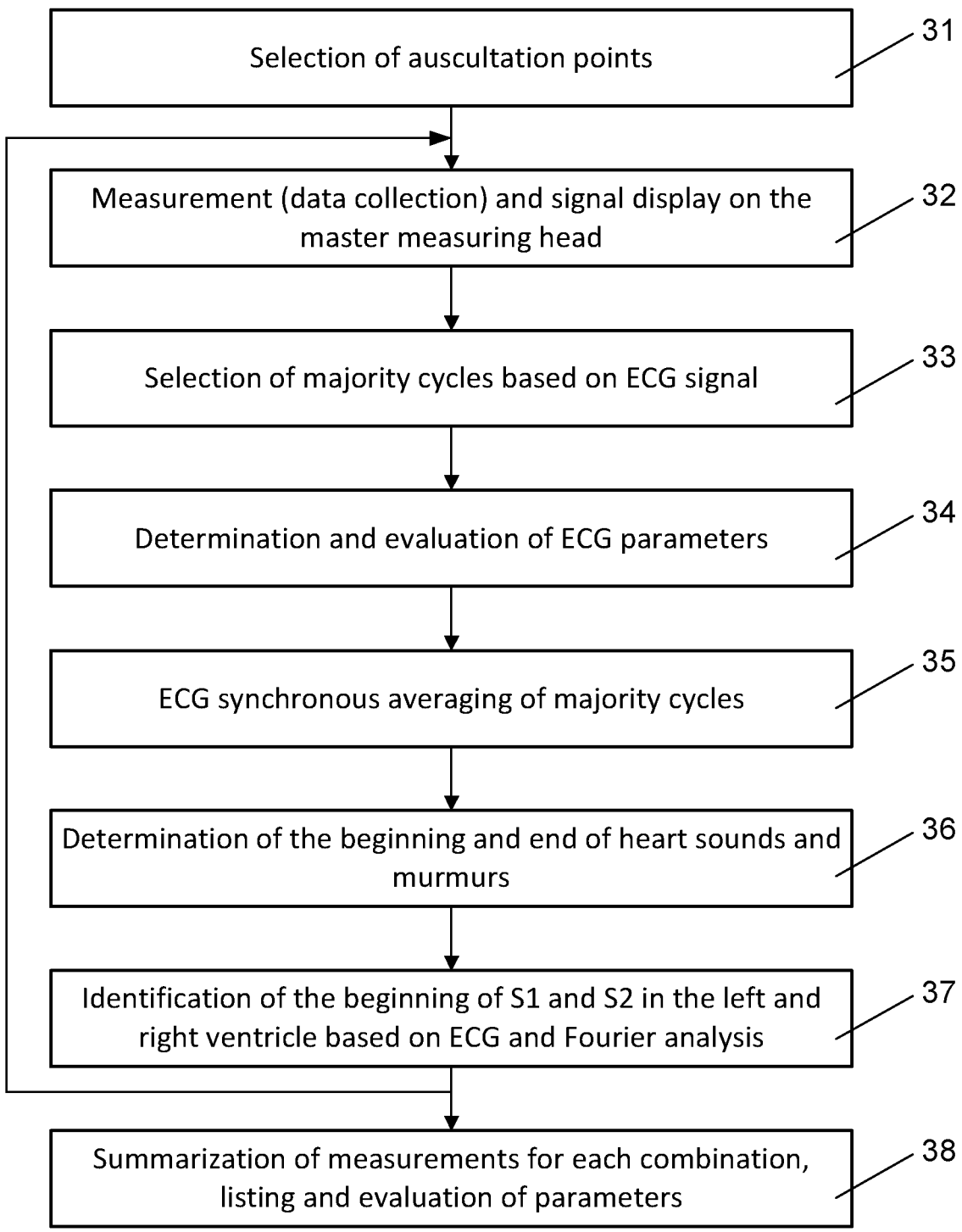
FIG. 7 shows the key steps of measurement performed with the measuring arrangement an evaluation.

In the description of the method according to the invention during the implementation which is only presented in FIG. 7 as an advantageous example, in step 31, the appropriate auscultation sites 9-12 are selected and the measuring heads 1 and 2 are placed onto the body surface 26 of the examined person. If the measuring heads 1, 2 are placed on the auscultation site over the mitral valve and over the aortic valve 10 as shown in FIG. 4, then the left ventricular signals of the first heart sound S1 and second heart sound S2 can be measured. Similarly, if the measuring heads 1, 2 are placed on the auscultation site over the tricuspid valve 11 and over the pulmonary valve 12 as shown in FIG. 4, then the right ventricular signals of the first heart sound S1 and second heart sound S2 can be measured. By placing measuring head 1 over auscultation site 9 and measuring head 2 over auscultation site 11, the difference between the S1 heart sound's left and right ventricular component can be detected.

Similarly, by placing measuring head 1 over auscultation site 12 and measuring head 2 over auscultation site 11, the difference between the S2 heart sound's left and right ventricular component can be detected. During the application of the invented combined measuring head, the master measuring head must be placed "above" the mitral valve because then the signal of the slave measuring head's ECG electrode will go to the phase inverting input of the amplifying stage 18 and the signal of the mitral valve's ECG electrode will go to the phase non-inverting input and thereby the recorded signal will be similar to a standard ECG II signal. And during the measurement of the right heart, the measured ECG becomes similar to the Y component of the Frank vector cardiogram. However, it is important that in both cases, we receive a sign which is convenient for the determination of the beginning of electronic activation/depolarization, that is the beginning of QRS interval which is considered as a point of reference in terms of evaluation and the determination of the end of the T wave, that is the end of repolarization and it can also be used for the detection of left or right bundle branch block, and by knowing it, the left and right ventricular components of the S1 heart sound can be identified.

In step 32 we perform data collection and its result is presented on the display placed on the master measuring head, following processing which is to be described in details later. In order to ensure the quality of data collection, the quality of signals to be recorded can be visually followed on the display.

During the processing, in step 33, majority cycles are selected based on the recorded ECG signal, where the selection of majority cycles takes places by comparing the recorded ECG signals by cycles. Here we examine the morphological similarity of the ±80 msec environment of the "fiducial-point", that is, the point with the steepest gradient by applying correlation coefficients. Of the developing clusters, the most populated cluster is considered as majority.

In step 34 the following ECG parameters are determined by thresholding procedure: Beginning of P wave, beginning and end of QRS, end of T wave, and RR distance (the reciprocal of heart rate). During the interpretation of S1 and S2, QRS width plays a role as it explains the delay of S1 or S2 compared to the beginning of Q wave.

In step 35, ECG synchronous averaging of the signal segments of the two PCG channels is performed. The data collection time is adjustable in each combination, but it is advisable to store a record of at least 30 seconds, approximately corresponding to 30 cardiac cycles. During the signal processing, it is expected, even in case of extra beats or noisy segments that there will be at least 25 majority cycles available for the improvement of signal-to-noise ratio by synchronous averaging, which results in an approximately five-fold increase of the root mean square of the signal-to-noise ratio.

In step 36 the border points, that is, the beginnings and ends of the heart sounds and murmurs will be determined. In case of the averaging of a PCG signal belonging to the n majority cycle, the root mean square of the sum of the partially overlapping signal and noise signals will tend to zero in a $1/n^{1/2}$ manner (where n stands for the number of heart cycles considered), at a point of the t time axis within the cardiac cycle which does not contain a J(t) heart sound signal yet or already, only noise Z(t) signal. Accordingly, advancing to the positive direction from the beginning of QRS, the $t_k$ value from which the root mean square caused by the averaging does not follow the $1/n^{1/2}$ rule, but stabilizes at a constant value near the value indicating noiselessness—this $t_k$ value is considered as the beginning (or end) of the heart sound signal. When determining the end of the heart sound signals, we follow the same principle as above, but to the opposite direction.

In case of both halves of the heart, determination of the beginning of the S1 and S2 heart sounds also form part of the processing, performed in step 37. The determination of these time points may take place by time-frequency (Fourier) analysis, exploiting the well-known fact that the vibration of the left heart has higher frequency components than that of the right heart. The obtained results are confirmed by the algorithm examining the QRS wave parameters of the ECG. According to the article of Oravetz et al in Circulation vol. 36, 275-283, in case of left bundle branch block and right bundle branch block, there is a significant shift in the beginning of S2 and in the timing of its components, which has a diagnostic significance. The referenced article includes the deviation of the two types of branch blocks from the normal case. For example in case of heart failure, the article of N de Oliveira Neto, et al.: "Abnormalities of the Systolic Time Intervals Obtained by Electronic Stethoscope in Heart Failure" provides data of interest in light of the change of systolic interval parameters.

In step 38, the processing program summarizes the measurements for the different measuring head placement combinations, lists the parameters and performs evaluation if needed.

During the method and the application of the measuring arrangement, the following information may be presented on the device which is connected to the measuring heads (1, 2) of the measuring arrangement—this may be a smartphone for example—for the professionals interested in the result of the analysis:

Recording all ECG signals belonging to the registration cycle, which the majority cycle determination is based upon. This service is only part of the detailed data recording, but it is not included in the short result provision.

A segment of the majority ECG cycle in each registration cycle, i.e. maximum 4 cycles lasting from the P wave on the ECG to the end of the next cycle's P wave (or equivalently from the QRS onset to the next cycle QRS onset), together with the simultaneously registered and averaged two PCG channels.

The vertical marker lines drawn above the registered and/or processed signals are visible, the beginning of P wave determined by the algorithm of the device (smartphone), the beginning and end of QRS wave, and the end of T wave are marked. The beginning and end of the examined patient's S1 and S2 wave and, if applicable, the beginning and end of murmurs will be presented on both averaged PCG channels.

For the sake of diagnostic evaluation, a different color is used for presenting the second marker line network typical of the healthy population, the left ventricular QS1 and QS2 interval (in medical terms, PEP and LVET) values, along with their typical band of standard deviation.

The above description shortly introduced the most essential data provision services made possible by the method according to the invention. An important characteristic of our invention is that the reference parameters of the S1 and S2 parameters which are the most important in terms of left ventricular function and which prevail in normal case (based on de Oliveira et al: The Internet Journal of Cardiology, 2007, vol. 5, No. 2), can be determined and presented on the display of the smartphone by the following regression correlations. These regression correlations are used for it:

$QS1=65-0.3\ HR=PEP$

The distance of heart sounds in healthy men:

$QS2=488-1.65\ HR, S1S2=428-1.35\ HR=LVET$

The distance of heart sounds in healthy women:

$QS2=553-2.3\ HR, S1S2=498-2.1\ HR=LVET$ where:
HR: heart rate,
PEP: left ventricular pre-ejection period,
LVET: left ventricular ejection time, The advantage of our recommended method is that it is suitable for patients of any physique, and can be matched well with the traditional auscultation practices of the physician. Compared to classic single measuring head/single sensor scanning, the difference here is that the scanning, performed during the auscultation which is part of the monitoring process, is carried out using two measuring heads that record the acoustic signals at two auscultation points as well as the ECG signal which is necessary for interpretation.

Another advantageous implementation mode of the present method allows the built-in processor of the device to determine the "majority cycles" (thus, extra beats or noisy beats are excluded from the processing) and derive the noise-reduced end result from their average or median.

A further advantage of the method is that the electromechanical cardiac cycle parameter range of the examined patient can be compared with the data of a healthy person by literature and thus perform a preliminary expert interpretation.

According to another advantageous implementation mode of the present method, the results are visually presented on the display panel of the smartphone (or another computing device), and an optional PCG signal may also be listened to in parallel upon request (e.g. for educational purposes).

A further advantage of the device is the wireless, e.g. Bluetooth data communication between the measuring head combination 1, 2 and the evaluating unit.

LIST OF REFERENCED SYMBOLS

M measuring unit
K evaluating unit
1 measuring head
2 measuring head
3, 4 electrode
3F electrode
5, 6 sensor
7 cable
8 display
9-12 auscultation site
13, 14 connector
15 R-R distance
16 QT distance
17 QRS onset
18 amplifying stage
19 amplifying stage
20 multiplexer stage
21 analog-to-digital converter
22 processing stage
23 memory stage
24 Bluetooth stage
25 battery
26 body surface
31-38 step
S1-S4 heart sound
J signal
Z murmur
t time

The invention claimed is:

1. A method for monitoring specific activity parameters of the human heart comprising the steps of:
 arranging measuring heads comprising electrodes of a measuring unit (M) on the chest of a patient;
 monitoring predetermined parameters by two measuring heads placed on the chest, wherein monitoring comprises capturing an electrocardiogram (ECG) signal by ECG electrodes and capturing a phonocardiogram (PCG) signal by PCG electrodes;
 transmitting the captured signals wirelessly from the measuring unit to a computing evaluating unit;
 evaluating transmitted signals by means of the computing evaluating unit, utilizing the captured ECG signal as a reference time for the PCG monitoring; and
 displaying at least one of captured signals and evaluation results with a display means of the computing evaluating unit,
 wherein the step of monitoring further comprises:
  performing monitoring the ECG and PCG signals simultaneously by two measuring heads, each comprising an ECG electrode and a PCG electrode, and
  operating one of the measuring heads as a master measuring head and the other one of the measuring heads as a slave measuring head and controlling operation of the slave measuring head by the master measuring head; and
 wherein monitoring is performed in the following order:
  capturing ECG and PCG signals between mitral (M) and aortic (Ao) auscultation points,
  capturing ECG and PCG signals between tricuspid (T) and pulmonic (AoPu) points, and
  determining a time difference between captured left and right ventricular mechanic contraction by capturing vibrations on the body surface between the Ao and AoPu points, then capturing vibrations on the body surface between the T and M points.

2. The method according to claim 1, wherein quality of the captured signal is displayed on a display of the master measuring head.

3. The method according to claim 1, wherein for exact determination of the electromechanical activity's time parameters, the parameters to be determined are derived from parameters of individuals considered healthy by literature standards and their synchronized, noise-reduced average.

4. The method according to claim 1, wherein a primary evaluation is conducted by using an expert service built into a smartphone in such a manner that the mechanical cardiac cycle parameters of the measured person are compared to the parameters of individuals considered healthy by literature standards and their standard deviation.

5. The method according to claim 1, wherein results are visually presented on the display means of the smartphone and simultaneously the PCG signals are made audible.

6. A measuring arrangement for monitoring specific activity parameters of the human body, the measuring arrangement comprising:
 a measuring unit including at least one measuring head comprising an electrocardiogram (ECG) sensor and at least one measuring head comprising a phonocardiogram (PCG) sensor; and
 an evaluating unit having a wireless communication connection with the measuring unit;
 wherein the measuring unit comprises two measuring heads designed as master and slave measuring heads each comprising more than one ECG electrode and PCG electrode, one of the measuring heads is operated as a master measuring head and the other one of the measuring heads is operated as a slave measuring head, the master measuring head provides control of the slave measuring head for performing simultaneous capturing of the hearts electromechanical activity; and
 wherein the master measuring head comprises a communication stage providing wireless communication with the evaluating unit;
 wherein the measuring heads comprise the electrodes for the bipolar ECG measurement in a distributed manner enabling a reference ECG measurement similar to a Lead II of 12-lead ECG system simultaneously with the left ventricular monitoring and data collection;
 wherein the ECG electrode of the master measuring head assigned for the auscultation point of the mitral valve is connected to an inverting input of an amplifying stage; and wherein a ground electrode is arranged on the master measuring head.

7. The measuring arrangement according to claim 6, wherein the measuring heads are interconnected by a multiconductor cable performing energy and signal transmission.

8. The measuring arrangement according to claim 7, wherein the cable has a length to allow a physician to carry the measuring arrangement comprising the two measurement heads hung on his/her neck.

* * * * *